US008778891B2

(12) United States Patent
Dal Farra et al.

(10) Patent No.: US 8,778,891 B2
(45) Date of Patent: Jul. 15, 2014

(54) DERMATOPONTIN-ACTIVATING PEPTIDES AND COSMETIC COMPOSITIONS INCLUDING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/884,412

(22) PCT Filed: Nov. 7, 2011

(86) PCT No.: PCT/FR2011/000591
§ 371 (c)(1),
(2), (4) Date: May 9, 2013

(87) PCT Pub. No.: WO2012/062977
PCT Pub. Date: May 18, 2012

(65) Prior Publication Data
US 2013/0288978 A1  Oct. 31, 2013

(30) Foreign Application Priority Data

Nov. 9, 2010 (FR) ..................................... 10 04380

(51) Int. Cl.
| | | |
|---|---|---|
| *A61K 38/08* | (2006.01) | |
| *A61K 38/10* | (2006.01) | |
| *A61K 8/64* | (2006.01) | |
| *C07K 7/06* | (2006.01) | |
| *C07K 7/08* | (2006.01) | |
| *A61Q 19/00* | (2006.01) | |
| *A61Q 19/08* | (2006.01) | |

(52) U.S. Cl.
CPC ... *C07K 7/06* (2013.01); *C07K 7/08* (2013.01); *A61Q 19/00* (2013.01); *A61Q 19/08* (2013.01); *A61K 38/08* (2013.01); *A61K 38/10* (2013.01); *A61K 8/64* (2013.01)
USPC ....... 514/21.8; 514/21.5; 514/21.6; 514/21.7; 514/18.8; 530/327; 530/328; 530/329; 530/330; 530/331

(58) Field of Classification Search
CPC .......... A61K 38/08; A61K 38/10; A61K 8/64; A61Q 19/00; A61Q 19/08; C07K 7/06; C07K 7/08
USPC ................... 514/18.8, 21.5, 21.6, 21.7, 21.8; 530/327, 328, 329, 330, 331
See application file for complete search history.

(56) References Cited

U.S. PATENT DOCUMENTS

| | | |
|---|---|---|
| 2005/0065089 A1 | 3/2005 | Ferree |
| 2008/0071706 A1 | 3/2008 | Honda et al. |
| 2010/0168126 A1 | 7/2010 | Ptchelintsev et al. |

FOREIGN PATENT DOCUMENTS

| | | |
|---|---|---|
| EP | 0503939 | 9/1992 |
| JP | 2008-201777 | 9/2008 |
| WO | 00/00214 | 1/2000 |
| WO | 2009/012472 | 1/2009 |

OTHER PUBLICATIONS

Definition of derivative, from http://cancerweb.ncl.ac.uk/omd/about.html, pp. 1-5. Accessed Jul. 7, 2005.*
Lewandowska, K. et al., "Extracellular matrix adhesion-promoting activities of a dermatan sulfate proteoglycan-associated protein (22K) from bovine fetal skin," Journal of Cell Science, 99, pp. 657-668 (1991).
MacBeath, J.R.E. et al., "Tyrosine-rich Acidic Matrix Protein (TRAMP) Accelerates Collagen Fibril Formation in Vitro," The Journal of Biological Chemistry, vol. 268, No. 26, pp. 19826-19832 (Sep. 15, 1993).
Okamoto, O. et al., "Dermatopontin interacts with transforming growth factor β and enhances its biological activity," Biochem. J., 337, pp. 537-541 (1999).
Takeda, U. et al., "Targeted Disruption of Dermatopontin Causes Abnormal Collagen Fibrillogenesis," The Journal of Investigative Dermatology, vol. 119, No. 3, pp. 678-683 (Sep. 2002).
PCT, International Search Report, International Application No. PCT/FR2011/000591 (mailed Jan. 19, 2012, published May 18, 2012).
Kullmann, "Proteases as Catalysts for Enzymic Syntheses of Opioid Peptides," The Journal of Biological Chemistry, vol. 255, No. 17, pp. 8234-8238 (Sep. 1980).
Kuroda, K. et al., "Dermatopontin Expression is Decreased in Hypertrophic Scar and Systemic Sclerosis Skin Fibroblasts and is Regulated by Transforming Growth Factor-β1, Interleukin-4, and Matrix Collagen," The Journal of Investigative Dermatology, vol. 112, No. 5, pp. 706-710 (May 1999).
Mayorov, A.V. et al., "Solid-phase peptide head-to-side chain cyclodimerization: Discovery of $C_2$-symmetric cyclic lactam hybrid α-melanocyte-stimulating hormone (MSH)/agouti-signaling protein (ASIP) analogues with potent activities at the human melanocortin receptors," Peptides, 31, pp. 1894-1905 (2010).
Ménard, R. et al., "The specificity of the $S_1$' subsite of cysteine proteases," FEBS Letters, vol. 328, No. 1,2, pp. 107-110 (Aug. 1993).
Okamoto, O. et al., "Dermatopontin Promotes Epidermal Keratinocyte Adhesion via α3β1 Integrin and a Proteoglycan Receptor," Biochemistry, vol. 49, No, 1, pp. 147-155 (2010).
Rovero, P. et al., "Structure-activity Relationship Study of R396, An $NK_2$ Tachykinin Antagonist Selective for the $NK_{2B}$ Receptor Subtype," Neuropeptides, 23, pp. 143-145 (1992).
Swedberg, J.E. et al., "Plasmin Substrate Binding Site Cooperativity Guides the Design of Potent Peptide Aldehyde Inhibitors," Biochemistry, 50, pp. 8454-8462 (2011).

* cited by examiner

Primary Examiner — Julie Ha
(74) Attorney, Agent, or Firm — Thompson Hine L.L.P.

(57) ABSTRACT

Peptides activating dermatopontin in the skin and cosmetic compositions including such peptide, in a physiologically suitable medium, are described. Methods of treating the cutaneous signs of aging and photoaging, and in particular wrinkles, sagging, and loss of volume and elasticity of the skin are also described.

16 Claims, No Drawings

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 1

Asp Arg Gln Trp
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 2

Asp Arg Glu Trp
1

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 3

Asp Arg Gln Trp Asn Tyr
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION

<400> SEQUENCE: 4

Arg Glu Trp Gln Phe Tyr Cys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION
<220> FEATURE:
<221> NAME/KEY: DISULFID
<222> LOCATION: (7)..(8)

<400> SEQUENCE: 5

Arg Glu Trp Gln Phe Tyr Cys Cys
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 6

Asp Arg Glu Trp Gln Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 7

Asp Arg Gln Trp Asn Tyr Ala Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MOD_RES
<222> LOCATION: (8)..(8)
<223> OTHER INFORMATION: AMIDATION
<220> FEATURE:
<221> NAME/KEY: DISULFID
<222> LOCATION: (8)..(9)

<400> SEQUENCE: 8

Asp Arg Gln Trp Asn Tyr Ala Cys Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 9

Asp Arg Glu Trp Gln Phe Tyr Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION
<220> FEATURE:
<221> NAME/KEY: DISULFID
<222> LOCATION: (8)..(9)

<400> SEQUENCE: 10

Asp Arg Glu Trp Gln Phe Tyr Cys Cys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 11

Asp Arg Gln Trp Lys Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 12
```

```
Arg Glu Trp Gln Phe Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Arg Glu Trp Gln Phe Tyr
1               5
```

DERMATOPONTIN-ACTIVATING PEPTIDES AND COSMETIC COMPOSITIONS INCLUDING SAME

RELATED APPLICATION DATA

This application is a National Stage filing of International Application No. PCT/FR2011/000591, filed Nov. 7, 2011, which claims the benefit of French Application No. 10 04380, filed Nov. 9, 2010.

FIELD OF THE INVENTION

This invention relates to the field of cosmetic and dermatopharmaceutical active principles as well as compositions comprising them.

This invention is intended to provide new molecules useful for preventing or fighting cutaneous signs of aging, and in particular wrinkles, sagging, and loss of volume and elasticity of the skin.

More specifically, the invention relates to peptides activating the expression of dermatopontin, cosmetic or pharmaceutical compositions containing such peptides, the use of such compositions to increase the expression of proteins of the extracellular matrix, and to prevent UV degradation of collagen fibers and elastic fibers and, finally, to cosmetic care methods intended to prevent and/or treat cutaneous signs of aging and photoaging.

BACKGROUND OF THE INVENTION

The skin is a covering organ comprised of a plurality of layers (dermis, dermoepidermal junction, epidermis). The dermis is the tissue supporting the skin and is comprised of water, elastin fibers and collagen fibers (70% of dermal fibers), enveloped in an interstitial matrix of proteoglycans. Fibroblasts are the main cellular component of the dermis and are the source of collagen fiber and elastin fiber synthesis.

The outermost part is the epidermis, a multistratified epithelium consisting essentially of keratinocytes closely linked to one another. The basal layer of the epidermis is comprised of a layer of proliferative cells, primarily keratinocytes and melanocytes, which are anchored on the dermoepidermal junction (DEJ). The DEJ is an extracellular network structure that constitutes the interface between the dermis and the epidermis.

The skin, like all other organs, is subjected to the complex physiological process of aging. Intrinsic or chronological aging, which is the consequence of genetically programmed senescence, is distinguished from biochemical alterations due to endogenous factors. In the skin, it is characterized by a slowing of the regeneration of cells and extracellular matrices, leading to dermal and epidermal atrophy, dryness, a reduction in elasticity, and the appearance of fine lines and wrinkles.

Extrinsic aging is due to environmental stresses to which the body is subjected throughout life, such as pollution, sun, diseases, lifestyle habits, and so on. Its effects are combined with those of intrinsic aging in areas chronically exposed to the sun; this is referred to as photoaging. The main alterations associated with photoaging are located at the dermis and include: the appearance of pigment spots, a reduction and fragmentation of collagen fibers causing wrinkles and the accumulation of dystrophic elastic fibers constituting solar elastosis.

Numerous avenues of research have been explored to identify active agents capable of fighting cutaneous aging, among which are protection from environmental stresses (sun, pollution, etc.), activation of cell regeneration, and reinforcement of the extracellular collagen and elastin matrix. This research has led to the market release of numerous more or less effective active agents. Therefore, it remains important to identify new compounds capable of preventing or fighting cutaneous aging. The problem more specifically targeted by the invention is that of fighting the disorganization of fibrillar structures of the skin's extracellular matrix that appear during aging or photoaging.

The inventors recently identified a beneficial molecular target to fulfill this function. It is dermatopontin, a small acid protein, rich in tyrosine, abundant in the dermis and more specifically around the collagen fibers. It plays a key role in the structuring of collagen fibrils (Jonathan et al., J. Biol. Chem., 1993, vol. 268, pp. 19826-19832), participates in the process of adhesion of fibroblasts (Lewandowska et al., J. cell Sci., 1991, vol. 99, pp. 657-668), keratinocytes via integrin $\alpha_3\beta_1$ and a proteoglycan-type receptor. These properties give dermatopontin an important role in healing (Akamoto et al., Biochem, 2010, vol. 49, pp. 147-155).

Confirming these results, the absence of dermatopontin in genetically modified mice results in a reduction in the thickness of the dermis and its collagen content, as well as in reduced elasticity of the skin (Takeda et al. J. Invest. Dermatol. 2002, vol. 119, pp. 678-683).

Independently of its structural role, dermatopontin can bind to decorin and TGF beta to form a trimeric complex and thus potentiate the action of TGF beta 1 (Okamoto et al., Biochem J. 1999 Feb. 1; 337 (3): 537-41).

The document JP2008-201777 discloses the use of peptides derived from dermatopontin, as agents promoting cell adhesion and healing.

The document US2005/0065089 discloses that native dermatopontin can be used to potentiate the activation of TGF beta in the context of a biological treatment of the disc herniations.

However, until now, no peptide according to the invention has been described for activating dermatopontin in the skin cells and preventing or repairing the skin signs of aging and photoaging.

DESCRIPTION OF THE INVENTION

The inventors have demonstrated that peptides with the following general formula (I):

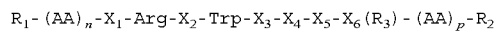

$$R_1-(AA)_n-X_1-\text{Arg}-X_2-\text{Trp}-X_3-X_4-X_5-X_6(R_3)-(AA)_p-R_2$$

are good dermatopontin-activating agents. Consequently, these peptides are suitable for fighting skin aging and photoaging.

The peptides according to the invention are characterized by the fact that they:
- activate dermatopontin expression,
- increase the expression of type-I and type-III collagen and fibronectin,
- prevent the degradation of fibrillar structures of collagen and elastic fibers in skin subjected to UV radiation.

The terms "peptide or active agent activating dermatopontin or capable of activating dermatopontin" refer to any peptide of general formula (I) capable of increasing the amount of dermatopontin present in the cell, either by increasing the protein synthesis by direct or indirect modulation of gene expression, or by other biological processes such as stabilization of the protein or stabilization of the messenger RNA transcriptions.

The term skin refers to all covering tissue forming the skin, the mucous membranes and the skin appendages, including the hair, the eyelashes and the eyebrows.

Thus, a first objective of the invention is to provide a peptide of general formula (I)

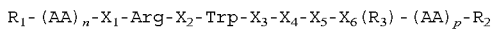

Wherein
$X_1$ represents aspartic acid or no amino acid,
$X_2$ represents glutamine or glutamic acid,
$X_3$ represents asparagine or lysine or glutamine or no amino acid,
$X_4$ represents phenylalanine or tyrosine or no amino acid,
$X_5$ represents tyrosine or alanine or no amino acid,
$X_6$ represents cysteine or no amino acid,
AA represents any amino acid and n and p are integers between 0 and 2;
$R_1$ represents the primary amine function of the N-terminal amino acid, free or substituted by a group of the acyl type (R—CO—) wherein the radical R is either a saturated or unsaturated $C_1$ to $C_{30}$ alkyl chain of the acetyl type, or an aromatic group of the benzoyl, tosyl, or benzyloxycarbonyl type;
$R_2$ represents the carboxyl function of the C-terminal amino acid having either a hydroxyl group free or substituted by a group chosen from a $C_1$ to $C_{30}$ alkyl chain or an —$NH_2$, —NHY or —NYY' group with Y and Y' representing a $C_1$ to $C_4$ alkyl chain;
$R_3$ represents the thiol function of cysteine in the $X_6$ position, either free or substituted by a methyl or an acetyl group, or covalently bound by a disulfide bond to another cysteine.

Said sequence of general formula (I) consists of 3 to 12 amino acid residues and can be in the form of salts.

According to an advantageous embodiment of the invention, the peptide preferably corresponds to the general formula (I)

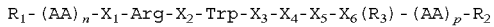

Wherein
$X_1$ represents aspartic acid or no amino acid,
$X_2$ represents glutamine or glutamic acid,
$X_3$ represents asparagine or lysine or glutamine or no amino acid,
$X_4$ represents phenylalanine or tyrosine or no amino acid,
$X_5$ represents tyrosine or alanine or no amino acid,
$X_6$ represents cysteine or no amino acid,
AA represents any amino acid with the exception of arginine, cysteine, leucine, glycine and glutamic acid; and n and p=0 or 1 with n different p;
$R_1$ represents the primary amine function of the N-terminal amino acid, free or substituted by a group of the acyl type (R—CO—) wherein the radical R is either a saturated or unsaturated $C_1$ to $C_{30}$ alkyl chain of the acetyl type, or an aromatic group of the benzoyl, tosyl, or benzyloxycarbonyl type;
$R_2$ represents the carboxyl function of the C-terminal amino acid having either a hydroxyl group free or substituted by a group chosen from a $C_1$ to $C_{30}$ alkyl chain or an —$NH_2$, —NHY or —NYY' group with Y and Y' representing a $C_1$ to $C_4$ alkyl chain;
$R_3$ represents the thiol function of cysteine in the $X_6$ position, either free or substituted by a methyl or an acetyl group, or covalently bound by a disulfide bond to another cysteine. Said sequence of general formula (I) consists of 3 to 7 amino acid residues and can be in the form of salt.

According to an especially preferred embodiment of the invention, the peptide has the sequence:

```
(SEQ ID No. 1):
Asp-Arg-Gln-Trp-NH2

(SEQ ID No. 2):
Asp-Arg-Glu-Trp-NH2

(SEQ ID No. 3):
Asp-Arg-Gln-Trp-Asn-Tyr-NH2

(SEQ ID No. 4):
Arg-Glu-Trp-Gln-Phe-Tyr-Cys-NH2

(SEQ ID No. 5):
Arg-Glu-Trp-Gln-Phe-Tyr-Cys(Cys)-(NH2)

(SEQ ID No. 6):
Asp-Arg-Glu-Trp-Gln-Phe-NH2

(SEQ ID No. 7):
Asp-Arg-Gln-Trp-Asn-Tyr-Ala-Cys-NH2

(SEQ ID No. 8):
Asp-Arg-Gln-Trp-Asn-Tyr-Ala-Cys(Cys)-(NH2)

(SEQ ID No. 9):
Asp-Arg-Glu-Trp-Gln-Phe-Tyr-Cys-NH2

(SEQ ID No. 10):
Asp-Arg-Glu-Trp-Gln-Phe-Tyr-Cys(Cys)-(NH2)

(SEQ ID No. 11):
Asp-Arg-Gln-Trp-Lys-Phe-NH2

(SEQ ID No. 12):
Arg-Glu-Trp-Gln-Phe-Tyr-NH2

(SEQ ID No. 13):
Arg-Glu-Trp-Gln-Phe-Tyr.
```

According to an especially beneficial embodiment, the peptide corresponds to the sequence SEQ ID No. 5.

According to another especially beneficial embodiment, the peptide corresponds to the sequence SEQ ID No. 9 or to SEQ ID No. 10.

According to another even more beneficial embodiment, the peptide corresponds to the sequence SEQ ID No. 12 or to SEQ ID No. 13.

The amino acids, constituting the peptide according to the invention and designated by the term AA, can be in any isomeric L- and D-configuration. Preferably, the amino acids are in L form.

The term "peptide" refers to a chain of two or more amino acids bound to one another by peptide bonds.

The term "peptide" also refers to the natural or synthetic peptide of the invention as described above, or at least one of its fragments, whether it is obtained by proteolysis or synthetically, or any natural or synthetic peptide of which the sequence consists entirely or partially of the sequence of the peptide described above.

To improve resistance to degradation, it may be necessary to use a protected form of the peptide according to the invention. Preferably, to protect the primary amine function of the N-terminal amino acid, a substitution with an $R_1$ group of the acyl type (R—CO—) is used, in which the radical R is either a saturated or unsaturated $C_1$ to $C_{30}$ alkyl chain of the acetyl type, or an aromatic group of the benzoyl, tosyl, or benzyloxycarbonyl type, even more preferably an acetyl group. Preferably, to protect the carboxyl function of the C-terminal amino acid, a substitution with an $R_2$ group of the $C_1$ to $C_{30}$ alkyl chain type, or an $NH_2$, NHY or NYY group with Y representing a $C_1$ to $C_4$ alkyl chain, even more preferably an $NH_2$ group, is used.

The peptide according to the invention can be protected at the N-terminal or C-terminal end or at both ends.

To inhibit the dimerization of the peptides according to the invention, the thiol function of the C-terminal cysteine can be substituted by a methyl or acetyl group, or another cysteine. In this last case, the substitution results in the formation of a disulfide bond between the two cysteine residues.

Thus, the invention relates to a composition as defined above, characterized in that the peptide according to the invention and advantageously with the sequence SEQ ID No. 1 to SEQ ID No. 13 is in protected form or not, preferably in protected form at the C-terminal end.

The peptide of general formula (I) according to the invention can be obtained either by classic chemical synthesis (in the solid phase or in the liquid homogeneous phase), or by enzymatic synthesis (Kullman et al. J. Biol. Chem., 1980, vol. 225, p. 8234) from constituent amino acids.

The peptide according to the invention can be of natural or synthetic origin. Preferably, according to the invention, the peptide is of synthetic origin, obtained by chemical synthesis.

According to the invention, the active agent can be a single peptide or a mixture of peptides.

The peptide according to the invention is advantageously solubilized in one or more physiologically suitable solvents, such as water, glycerol, ethanol, propanediol, butylene glycol, dipropylene glycol, the ethoxylated or propoxylated diglycols, the cyclic polyols or any mixture of these solvents.

The term "physiologically suitable" means that the solvent chosen is suitable for coming into contact with the skin without causing toxicity or intolerance reactions.

The diluted peptide is then sterilized by sterile filtration.

After this dilution step, the peptide can be encapsulated or contained in a cosmetic or pharmaceutical vector such as liposomes or any other microcapsule used in the cosmetic field or adsorbed on powdery organic polymers, mineral carriers such as talcs and bentonites, and more generally solubilized in, or bonded to, any physiologically suitable vector.

According to a second subject matter of the invention, the peptide of general formula (I) can be used as a drug.

Especially advantageously, the peptide of general formula (I) can be used as a healing agent.

Another objective of the invention is to provide a pharmaceutical healing composition including, in a physiologically suitable medium, the peptide according to the invention.

According to a specific aspect of the invention, said peptide can be used to treat dermatological symptoms associated with age or premature photoaging, and in particular delayed healing, laxness and dermal atrophy, solar elastosis and reduced dermoepidermal cohesion.

Advantageously, according to this embodiment of the invention, the pharmaceutical compositions will be suitable for topical use or may be in a suitable liquid form for injection below or in the skin, in particular suitable for multiple superficial local mesotherapy-type injections.

A third objective of the invention is to provide a cosmetic composition including, in a physiologically suitable medium, a peptide of general formula (I), as a dermatopontin-activating agent.

According to an advantageous embodiment of the invention, the active agent according to the invention is present in the compositions of the invention at a concentration of between around $10^{-9}$ M and $10^{-3}$ M, and preferably at a concentration of between $10^{-8}$ M and $10^{-5}$ M, and even more preferably between $5\times10^{-5}$ M and $5\times10^{-6}$ M with respect to the total weight of the final composition.

This range of concentrations represents the necessary amount of active agent to obtain the desired molecular effect, namely, activating the expression of dermatopontin, type-I and type-III collagen and fibronectin.

Preferably, the composition according to the invention is in a form suitable for topical application including a medium that is physiologically suitable for the skin. "Physiologically suitable" refers to media that are suitable for use in contact with the skin or the human skin appendages, without the risk of toxicity, incompatibility, instability, allergic response or other adverse effects.

"Topical application" refers to the application or spreading of the active agent according to the invention, or a composition containing it, on the surface of the skin.

These compositions may in particular be in the form of an aqueous, hydro-alcoholic or oily solution; an oil-in-water or a water-in-oil emulsion or multiple emulsions; aqueous or anhydrous gel; colloid. These compositions can also be in the form of creams, suspensions, or powders, suitable for application on the skin, mucous membranes, lips and/or skin appendages. These compositions may be more or less fluid and have the appearance of a cream, a lotion, a milk, a serum, a pomade, a cream, a paste or a foam. They may also be in solid form, such as a stick, or be applied to the skin in aerosol form. They may be used as a care product and/or as a make-up product for the skin.

All of these compositions include, in addition, any additive commonly used in the field of use envisaged as well as the adjuvant necessary for their formulation, such as co-solvents (ethanol, glycerol, benzyl alcohol, humectant, etc.), thickening agents, diluents, emulsifiers, antioxidants, coloring agents, sunscreens, pigments, fillers, preservatives, perfumes, odor absorbents, essential oils, trace elements, essential fatty acids, surfactants, film-forming polymers, chemical or mineral filters, hydrating agents or thermal water, and so on. It is possible, for example, to cite water-soluble polymers of a natural type, such as polysaccharides, or polypeptides, cellulosic derivatives of the methylcellulose or hydroxypropyl cellulose type, or synthetic polymers, poloxamers, carbomers, siloxanes, PVA or PVP, and in particular polymers sold by the ISP company.

In any case, a person skilled in the art will make sure that these adjuvants as well as their proportions are chosen so as not to counteract the advantageous properties sought in the composition according to the invention. These adjuvants may, for example, be present in concentrations ranging from 0.01 to 20% of the total weight of the composition. When the composition of the invention is an emulsion, the fatty phase may represent 5 to 80% by weight and preferably 5 to 50% by weight with respect to the total weight of the composition. The emulsifiers and co-emulsifiers used in the composition will be chosen from those conventionally used in the field considered. For example, they can be used in a proportion ranging from 0.3 to 30% by weight, with respect to the total weight of the composition.

Of course, the active agent according to the invention can be used alone or in association with other active agents.

Advantageously, the compositions that can be used according to the invention contain, in addition, at least one other active agent intended to reinforce the action of the active agent according to the invention, in the field of preventing and improving skin signs of aging, or another active agent making it possible to expand the range of properties of the composition considered.

It is possible to cite, in a non-limiting manner, the following classes of ingredients: regenerating, anti-aging, anti-wrinkle, thickening, anti-free radical, anti-glycation, hydrating, antibacterial, antifungal, keratolytic, muscle relaxing, exfoliating, and toning agents, agents stimulating the synthesis of dermal macromolecules or energy metabolism, agents modulating cutaneous differentiation, pigmentation or depigmentation, agents stimulating nail or hair growth, agents stimulating microcirculation, sunscreens or metalloproteinase-inhibiting agents.

In a particular embodiment of the invention, the composition according to the invention will also include, aside from the peptide according to the invention,

- at least one cytochrome c-activating compound, and/or
- at least one hydrating compound, such as an aquaporin-activating compound, and/or
- at least one sirtuin-activating compound, and/or
- at least one cell adhesion-increasing compound, and/or
- at least one compound that increases the production of matrix proteins such as collagen, fibronectin, laminin, glycosaminoglycans, and/or
- at least one proteasome activity-modulating compound, and/or
- at least one circadian rhythm-modulating compound, and/or
- at least one HSP protein-modulating compound, and/or
- at least one cellular energy-increasing compound, and/or
- at least one skin pigmentation-modulating compound, and/or
- at least one coenzyme Q10-activating compound, and/or
- at least one compound improving the barrier function, such as a transglutaminase or HMG-CoA reductase-activating compound, and/or
- at least one mitochondria-protecting compound.

Said above compounds may be of natural origin, such as peptide hydrolysates of plants, or of synthetic origin, such as peptides.

Independently of their functions, the other active agents associated with the active agent according to the invention in the composition may have very diverse chemical structures. It is possible to cite, in a non-limiting manner, peptides, vitamin C and derivatives thereof, B-group vitamins, DHEA (dihydroepiandrosterone), phytosterols, salicylic acid and derivatives thereof, retinoids, flavonoids, sugar amines, azoles, metal salts, peptide extracts of plant origin or polymers.

A fourth objective of the invention concerns the use of a cosmetic composition, including the peptide of general formula (I) as an active agent, to reinforce the structure of the dermoepidermal junction, stimulate the expression of components of the dermoepidermal junction, increase the densification of the area supporting the dermoepidermal junction, or even improve the anchoring of basal keratinocytes and/or melanocytes to the dermoepidermal junction.

A fifth objective of the invention concerns the use of a cosmetic composition including the peptide of general formula (I) as an active agent, in order to increase the expression of proteins of the extracellular matrix by the fibroblasts of the skin.

According to an advantageous aspect of the invention, the active agent makes it possible to increase the density and elasticity of the dermis, and therefore the firmness of the skin, prevent or fight sagging of the lines of the face, loss of volume, thinning of the skin, atony, fine lines, deep wrinkles and dermal atrophy.

A sixth objective of the invention concerns the use of a cosmetic composition, including the peptide of general formula (I) as an active agent, in order to prevent the degradation of collagen fibers and elastic fibers in the skin subjected to external stresses.

The term "external stresses" refers to stresses that can be produced by the environment. For example, it is possible to cite stresses such as pollution, UV radiation, or irritants. Pollution refers both to "external" pollution due, for example, to diesel particles, ozone or heavy metals, and "internal" pollution, which may be due in particular to emissions from paint solvents, glues, or wallpapers (such as toluene, styrene, xylene or benzaldehyde), or cigarette smoke.

It has been demonstrated that the active agent makes it possible to limit degradation and disorganization of elastic fibers and to stimulate the reorganization of collagen fibers after UV radiation, and more specifically UVA radiation.

The disorganization of elastic fibers refers to all modifications due to repeated exposure to the sun, as well as the accumulation of dystrophic elastic fibers typical of solar elastosis. These alterations, which are difficult to reverse and partially responsible for age-related cutaneous ptosis or sagging, are due primarily to UVA radiation which deeply penetrate the dermis.

A specific embodiment of the invention relates to the use of a cosmetic composition including the peptide according to the invention, to prevent or fight unaesthetic signs related to solar elastosis and/or disorganization of elastic fibers caused by exposure to UV radiation, and more specifically UVA radiation.

A seventh objective of the invention concerns the use of a cosmetic composition including the peptide of general formula (I) as an active agent to increase the regeneration of the epidermis and the dermis.

The phrase "regeneration of the epidermis and the dermis" means that, according to this advantageous aspect of the invention, the peptide of the invention causes a greater proliferation and migration of the keratinocytes and fibroblasts, thereby promoting accelerated renewal of the epidermis and more generally better regeneration of the skin.

An eighth objective of the invention concerns a method for cosmetic care intended to prevent and/or treat cutaneous signs of aging and photoaging, characterized in that a composition according to the invention is applied topically to the skin to be treated.

The expression "cutaneous signs of aging" refers to all modifications of the exterior appearance of the skin and skin appendages due to aging, such as, for example, thinning of the skin, sagging, loss of elasticity and atony, deep lines and wrinkles, loss of firmness and tone, dermal atrophy or any other internal degradation of the skin resulting from exposure to UV radiation.

In particular, the invention relates to a method for cosmetic treatment intended to protect the skin from stresses due to UV radiation.

In one specific embodiment, the composition is applied before exposure to the sun, as a pre-sun care treatment to prevent disorganization of the elastic fibers.

In a second embodiment of the invention, the composition is applied after sun exposure, as an after-sun care treatment to repair damage suffered by collagen and elastic fibers.

Other advantages and features of the invention will become clearer in view of the following examples provided for illustrative and non-limiting purposes.

Example 1

Demonstration of the Activating Effect of SEQ ID No. 5 and SEQ ID No. 9 Peptides on the Expression of Dermatopontin The objective of this study is to determine the influence of the SEQ ID No. 5 peptide and of the SEQ ID No. 9 peptide on the expression of dermatopontin in fibroblasts. For this, specific immunofluorescence labelings were performed on normal human fibroblast cultures and on skin kept in culture ex vivo.

Protocol:

Normal human fibroblasts are cultivated for 24 or 48 hours and treated once daily with a $10^{-6}$M solution of peptide SEQ ID No. 5 or of peptide SEQ ID No. 9. The cells are then washed and fixed with 3.7% formaldehyde for 10 minutes at ambient temperature.

The human skin samples are placed in culture at the air/liquid interface. A $10^{-6}$M solution of peptide SEQ ID No. 5 or of peptide SEQ ID No. 9 is applied topically, then the samples are incubated for 24 hours or 48 hours. These skin samples are then fixed with formaldehyde then embedded in paraffin or fixed with OCT, by freezing at $-20°$ C. Sections of 3 to 4 µm are then produced (6 µm for the cold sections). The immunolabeling of the samples embedded in paraffin is performed after unmasking specific sites. The immunolabeling of samples embedded in OCT is performed after fixation at 37° C. and with cold acetone.

The fixed cells or the sections are incubated in the presence of a specific rabbit dermatopontin polyclonal antibody (Proteintech group, Ref: 10537-1-AP), then a secondary antibody, coupled to a fluorescent marker. After mounting in an ad hoc medium, the cells are then examined with an Epi-fluorescence microscope (Nikon Eclipse E600 microscope).

Results:

Under all of the conditions tested, more intense fluorescence is observed in the fibroblasts treated by the SEQ ID No. 5 peptide or the SEQ ID No. 9 peptide at $10^{-6}$ M than under the control conditions.

Human skin shows more intense fluorescence at the dermis in samples treated with the SEQ ID No. 5 peptide or the SEQ ID No. 9 peptide.

Conclusions:

The SEQ ID No. 5 and SEQ ID No. 9 peptides very substantially stimulate the expression of dermatopontin by the fibroblasts of the dermis.

Example 2

Study of the Ultrastructure of Cutaneous Cells Treated with the SEQ ID No. 5 Peptide The objective of this study is to observe the subcellular structures of keratinocytes and fibroblasts treated by the SEQ ID No. 5 peptide at $10^{-6}$ M.

Protocol:

NHEK or fibroblasts are cultivated in a dish or in a Transwell system, or skins cultivated ex vivo are treated with a $10^{-6}$ M solution of SEQ ID No. 5 peptide for 48 hours (the medium is changed every 24 hours). The skin cells or samples are washed with PBS, then are fixed by Karnosky hypertonic fixation (4% paraformaldehyde, 5% glutaraldehyde in a 0.08M phosphate buffer), 1 hour at ambient temperature, 24 hours at 4° C. The cells are detached from the substrate by scraping, centrifuged for 5 minutes at 1000 rpm at 4° C. The supernatant is removed and a 0.1 M sodium cacodylate buffer is deposited on the pellet. The cells are mixed with 2% agar then post-fixed by osmium tetroxide for 1 hour. The specimens are then dehydrated by successive passages in an alcohol series (50 to 100%). The skin cells or samples are then coated with a resin. The polymerization is performed for around 12 hours at 60° C. Semi-fine sections of 0.5 µm are performed with the ultra-microtome. The sections are deposited on a subbed slide under heat then stained with toluidine blue. The slides are then dehydrated again and mounted in a suitable medium. After the optimal study area has been chosen, the block is resized to the desired size and ultrafine sections are produced. Only the sections that have a "silver-gray" color and a suitable size are mounted on the electronic microscopy grid double-labeled with uranyl acetate and lead citrate, and are examined with the transmission microscope at 60 or 80 KV.

Results:

The ultrastructural study shows an enrichment in organelles, and in particular mitochondria in the keratinocytes treated by the SEQ ID No. 5 peptide. In cultures in a TRANSWELL® system, the intercellular contacts between the keratinocytes appear to be more cohesive and the interdigitations appear to be more stained than the untreated control Similarly, in ex vivo skin cultures, narrower cellular contacts between the cells of the basal layer are observed.

In the fibroblasts in culture treated by the SEQ ID No. 5 peptide, it is observed that the caveolar bodies, the rough endoplasmic reticulum and the Golgi apparatus are substantially more developed than in the control cells. A more intense secretion of components of the extracellular matrix is also observed by comparison with the untreated control cells.

Conclusions:

In the keratinocytes in culture, the SEQ ID No. 5 peptide at $10^{-6}$ M causes a general stimulation of cellular activity with, in particular, an increase in the density of mitochondria.

In the fibroblasts, the SEQ ID No. 5 peptide induces an increase in the synthesis of components of the extracellular matrix.

In ex vivo skin cultures, the SEQ ID No. 5 peptide increases the intercellular contacts of the basal keratinocytes.

Example 3

Demonstration of the Activating Effect of the SEQ ID No. 5 Peptide on the Expression of Fibronectin The objective of this study is to determine the influence of the SEQ ID No. 5 peptide on the expression of fibronectin, a protein of the extracellular matrix synthesized by the fibroblasts. For this, specific immunofluorescence labelings were performed on fibroblast cultures and on ex vivo skin cultures.

Protocol:

Human dermal fibroblasts in culture are treated once daily with a $10^{-6}$ solution M of SEQ ID No. 5 peptide (the medium containing the active agent is changed every 24 hours). The cells are then washed and fixed with 3.7% formaldehyde for 10 minutes at ambient temperature.

The human skin samples are placed in culture at the air/liquid interface. A $10^{-6}$ M solution SEQ ID No. 5 peptide or SEQ ID No. 9 peptide is to be applied topically, then the samples are incubated for 24 or 48 hours. These skin samples are then fixed with formaldehyde, then embedded in paraffin or fixed with OCT by freezing at $-20°$ C. Sections of 3 to 4 µm are then produced (6 µm for cold sections). The immunolabeling of the samples embedded in paraffin is performed after unmasking specific sites. The immunolabeling of the samples embedded in OCT is performed after fixation at 37° C. and with cold acetone.

The fixed cells or the sections are incubated in the presence of a specific rabbit fibronectin polyclonal antibody (Sigma, Ref: F-3648), then a secondary antibody, coupled with a fluorescent marker. The cells are then examined with the Epi-fluorescence microscope (Nikon Eclipse E600 microscope).

Results:

A more intense cytoplasmic fluorescence is observed in the fibroblasts treated with the SEQ ID No. 5 peptide at $10^{-6}$M than in the control cells.

In the ex vivo skin, the fluorescence is located primarily in the upper portion of the papillary dermis, immediately below the dermoepidermal junction.

Conclusions:

The SEQ ID No. 5 peptide very substantially stimulates the expression of fibronectin in the fibroblasts.

In the human skin, the SEQ ID No. 5 peptide stimulates the densification of the area supporting the dermoepidermal junction.

Example 4

Demonstration of the Activating Effect of the SEQ ID No. 5 Peptide on the Expression of Molecules of the Collagen I and Collagen III Dermal Extracellular Matrix The objective of this study is to determine the influence of the SEQ ID No. 5 peptide on the expression of molecules of the dermal extracellular matrix. For this, the expression of collagens I and III in human fibroblasts obtained from the dermis was studied.

Protocol:

Normal human fibroblasts are cultivated for 24 or 48 hours and treated once per day with a $10^{-6}$M solution of SEQ ID No. 5 peptide or SEQ ID No. 9 peptide. The cells are then washed and fixed with formaldehyde at 3.7% for 10 minutes at ambient temperature.

The human skin samples are placed in culture at the air/liquid interface. A $10^{-6}$M solution of SEQ ID No. 5 peptide or SEQ ID No. 9 peptide is applied topically, then the samples are incubated for 24 hours or 48 hours. These skin samples are then fixed with formaldehyde, then embedded in paraffin or fixed with OCT by freezing at −20° C. Sections of 3 to 4 μm are then produced (6 μm for cold sections). The immunolabeling of samples embedded in paraffin is performed after unmasking specific sites. The immunolabeling of the samples embedded in OCT is performed after fixation at 37° C. and with cold acetone.

The fixed cells or sections are incubated in the presence of a specific rabbit collagen I polyclonal antibody (Rockland, Ref: 600-401-103) or a specific rabbit collagen III polyclonal antibody (Rockland, Ref: 600-401-105), then a secondary antibody coupled to a fluorescent marker. After mounting in an ad hoc medium, the cells are then examined with the Epi-fluorescence microscope (Nikon Eclipse E600 microscope).

Results:

A more intense fluorescence is observed in the cultures and on the skin sections treated with the SEQ ID No. 5 peptide at $10^{-6}$M than under the control conditions.

Conclusions:

The SEQ ID No. 5 peptide at $10^{-6}$M increases the expression of collagen I and collagen III, two essential fibrillar proteins of the dermal extracellular matrix.

Example 5

Demonstration of the Protective Effect of the SEQ ID No. 5 Peptide on Elastin Fibers Subjected to UV Irradiation The objective of this study is to determine the influence of the SEQ ID No. 5 peptide on the elastic fibers present in the dermis. To do this, specific staining of the elastic fibers was performed on skin samples cultivated ex vivo.

Protocol:

Human skin samples are placed in culture at the air/liquid interface. A $10^{-6}$ M solution of SEQ ID No. 5 peptide is applied topically, then the samples are incubated for 48 hours before being irradiated by UVA at 5 J/cm². Untreated irradiated controls are produced in parallel.

These skin samples are then fixed with formaldehyde, then embedded in paraffin. Sections of 4 μm are then produced. These skin sections are successively removed from the paraffin, then rehydrated in different xylene and alcohol baths. the elastin fibers are stained using an Elastika van Gieson staining kit (VWR, Ref: 1.15974). The stained skin sections are dehydrated then mounted in the Eukitt mounting medium and observed under a microscope.

Results:

The observations under a microscope show less degradation of the elastic fibers, as well as better preservation of the organization of the elastic fibers in the samples irradiated and treated by the SEQ ID No. 5 peptide at $10^{-6}$M than under the control conditions.

Conclusion:

The SEQ ID No. 5 peptide at $10^{-6}$M preserves the elastic fibers of the alterations caused by UV radiation.

Example 6

Demonstration of the Regenerating Effect of the SEQ ID No. 5 Peptide

The objective of this study is to determine the regenerating effect of the SEQ ID No. 5 peptide on dermal fibroblasts and normal human keratinocytes (NHEK). To do this, the Ibidi in vitro healing model (Integrated Bio Diagnostics, Munich, Germany) was used.

Protocol:

This test consists of maintaining a cell-free area at the middle of a cell layer and of evaluating the time taken by the cells arranged on either side of the "scar" to migrate or proliferate and fill the gap. The self-adhesive silicone culture inserts are placed at the base of a well of a culture plate. These inserts have the special feature of being comprised of two distinct chambers separated by an impermeable membrane with a thickness of 500 μm. Each of the two chambers is seeded with cells of the same cell type and cultivated until confluency. The insert is then removed with sterile tweezers, creating an acellular area 400 μm wide between the two cell layers. The cells are then treated with a $10^{-6}$ M or a $3 \times 10^{-6}$M solution of SEQ ID No. 5 peptide added to the culture medium, with renewal of the peptide every 24 hours. Phase-contrast microscopy observations (Olympus CK40 microscope X5 connected to an Olympus E-510 camera) were performed at different times (0, 6, 24, 30 and 48 hours) until the proliferation and migration process results in the filling of the gap.

Results:

The microscopic observations show total filling of the gap after 30 hours by the human keratinocytes treated with the SEQ ID No. 5 peptide at $10^{-6}$ M. At the same time, under the control conditions, the cellular gap has not yet been filled.

The total filling of the gap appears after 48 hours for the human fibroblasts treated with the SEQ ID No. 5 peptide at $10^{-6}$ M. At the same time, under control conditions, the cellular gap has not yet been filled.

The effect of the peptide is dose-dependant, since the gap fills faster when the cells are treated with SEQ ID No. 5 at $3\times10^{-6}$ M.

Conclusions:

The fibroblasts and normal human keratinocytes (NHEK) filled the gap faster when they were cultivated in the presence of the SEQ ID No. 5 peptide, by comparison with control conditions.

The SEQ ID No. 5 peptide stimulates the proliferation and migration of fibroblasts and NHEK, thus promoting skin regeneration.

Example 7

Preparation of Compositions

1—Sun Protection Cream:

| Trade names | INCI names | weight % |
| --- | --- | --- |
| PHASE A | | |
| Demineralized water | Aqua (Water) | qsf |
| PEMULEN ™ TR-1 | Acrylates/C10-30 Alkyl Acrylate Crosspolymer | 0.40 |
| Glycerin | Glycerin | 3.00 |
| NIPASTAT ® Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| PARSOL ® MCX | Ethylhexyl Methoxycinnamate | 7.50 |
| EUSOLEX ® 4360 | Benzophenone-3 | 3.00 |
| PARSOL ® 1789 | Butyl Methoxydibenzoylmethane | 2.00 |
| MYRITOL ® 318 | Caprylic/Capric Triglyceride | 4.00 |
| EMULGADE ® SEV | Hydrogenated Palm Glycerides (and) Ceteareth-20 (and) Ceteareth-12 (and) Cetearyl Alcohol | 5.00 |
| Propylparaben | Propylparaben | 0.15 |
| NACOL ® 16-98 | Cetyl Alcohol | 1.00 |
| PHASE C | | |
| TEA | Triethanolamine | 0.20 |
| PHASE D | | |
| SEQ ID No. 5 peptide | | $3\times10^{-6}$ M |
| Fragrance | Fragrance | qsf |
| Coloring agent | | qsf |

The constituents of phase A and phase B are heated separately at between 70° C. and 75° C. Phase B is emulsified in phase A under agitation. Phase C is added at 45° C. by increasing the agitation. Phase D is then added when the temperature is below 40° C. The cooling is continued until 25° C. under active agitation.

2—Facial Sculpting Cream:

| Trade names | INCI names | weight % |
| --- | --- | --- |
| Phase A | | |
| MONTANOV ™ 68 | Cetearyl Alcohol (and) Cetearyl Glucoside | 6.00 |
| Squalane | Squalane | 3.00 |
| CETIOL ® SB 45 | *Butyrospermum Parkii* (Shea Butter) | 2.00 |
| Waglinol 250 | Cetearyl Ethylhexanoate | 3.00 |
| AMERCHOL ™ L-101 | Mineral Oil (and) Lanolin Alcohol | 2.00 |
| ABIL ® 350 | Dimethicone | 1.50 |
| BHT | BHT | 0.01 |
| Coenzyme Q10 | Ubiquinone | 0.10 |
| Phase B | | |
| Avocado oil | *Persea Gratissima* (Avocado) Oil | 1.25 |
| PHENONIP ® | Phenoxyethanol (and) Methylparaben (and) Ethylparaben (and) Butylparaben (and) Propylparaben (and) Isobutylparaben | 0.75 |
| Phase C | | |
| Demineralized water | Aqua (Water) | qsf |
| Butylene Glycol | Butylene Glycol | 2.00 |
| GLUCAM ™ E10 | Methyl Gluceth-10 | 1.00 |
| Allantoin | Allantoin | 0.15 |
| CARBOPOL ® Ultrez 10 | Carbomer | 0.20 |
| Phase D | | |
| TEA | Triethanolamine | 0.18 |
| Phase E | | |
| Peptide SEQ ID No. 5 | | $1\times10^{-6}$ M |
| GP4G | Water (and) Artemia Extract | 1.50 |
| Collaxyl | Water (and) Butylene Glycol (and) Hexapeptide-9 | 3.00 |
| Phase F | | |
| Fragrance | Fragrance | qsf |
| Coloring agent | | qsf |

Prepare and melt phase A at 65-70° C. Heat phase C to 65-70° C. Phase B is added to phase A just before A is emulsified in B. At around 45° C., the carbomer is neutralized by adding phase D. Phase E is then added under slight agitation and the cooling is continued until 25° C. Phase F is then added if desired.

3—Daytime Protective Cream:

| Trade names | INCI names | weight % |
| --- | --- | --- |
| Phase A | | |
| EMULIUM ® Delta | Cetyl alcohol (and) Glyceryl Stearate (and) PEG-75 Stearate (and) Ceteth-20 (and) Steareth-20 | 4.00 |
| LANETTE ® O | Cetearyl Alcohol | 1.50 |
| D C 200 Fluid/100 cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| CEGESOFT ® PS6 | Vegetable Oil | 1.00 |
| Vitamin E | Tocopherol | 0.30 |
| PHENONIP ® | Phenoxyethanol (and) Methylparaben (and) Ethylparaben (and) Butylparaben (and) Propylparaben (and) Isobutylparaben | 0.70 |

-continued

| Trade names | INCI names | weight % |
|---|---|---|
| Phase B | | |
| Demineralized water | Aqua | qsf 100 |
| Glycerin | Glycerin | 2.00 |
| CARBOPOL ® EDT 2020 | Acrylates/C10-30 Alkyl Acrylate Crosspolymer | 0.15 |
| KELTROL ® BT | Xanthan Gum | 0.30 |
| Phase C | | |
| Sodium Hydroxide (10% sol.) | Sodium Hydroxide | 0.30 |
| Phase D | | |
| Demineralized water | Aqua | 5.00 |
| STAY-C ® 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) Artemia Extract | 1.00 |
| Peptide SEQ ID No. 9 | | $2 \times 10^{-6}$ M |

Prepare phase A and heat to 75° C. under agitation. Prepare phase B by dispersing the carbopol, then the xanthan gum under agitation. Let sit. Heat to 75° C.

At temperature, emulsify A in B under rotor-stator agitation. Neutralize phase C under rapid agitation. After cooling at 40° C., add phase D, then phase E. The cooling is continued under slight agitation and phase F is added.

Applicants incorporate by reference the material contained in the accompanying computer readable Sequence Listing entitled "US10-146_ST25.txt", which was created on May 2, 2013, and is 3,430 bytes in size.

The invention claimed is:

1. A peptide of general formula (I):

$$R_1\text{-}(AA)_n\text{-}X_1\text{-}Arg\text{-}X_2\text{-}Trp\text{-}X_3\text{-}X_4\text{-}X_5\text{-}X_6(R_3)\text{-}(AA)_p\text{-}R_2$$

wherein, $X_1$ is aspartic acid or absent,
$X_2$ is glutamine or glutamic acid,
$X_3$ is asparagine or lysine or glutamine or absent,
$X_4$ is phenylalanine or tyrosine or absent,
$X_5$ is tyrosine or alanine or absent,
$X_6$ is cysteine or absent,
AA is any amino acid and n and p are integers between 0 and 2,
$R_1$ is the primary amine function of the N-terminal amino acid, free or substituted by a group of the acyl type (R—CO—) wherein the radical R is either a saturated or unsaturated $C_1$ to $C_{30}$ alkyl chain of the acetyl type, or an aromatic group of the benzoyl, tosyl, or benzyloxycarbonyl type,
$R_2$ is the hydroxyl group of the carboxyl function of the C-terminal amino acid, substituted by a group chosen from a $C_1$ to $C_{10}$ alkyl chain, or an $NH_2$, NHY or NYY group with Y representing a $C_1$ to $C_4$ alkyl chain or one of the salts thereof,
$R_3$ is the thiol function of cysteine in the $X_6$ position, wherein the thiol function is free or substituted by a methyl group or an acetyl group, or the thiol function is covalently bound by a disulfide bond to another cysteine;
with the proviso that when $X_1$ is absent, n is 0.

2. The peptide of claim 1, wherein said peptide of general formula (I) is

Asp-Arg-Gln-Trp-NH$_2$, (SEQ ID NO: 1)

Asp-Arg-Glu-Trp-NH$_2$, (SEQ ID NO: 2)

Asp-Arg-Gln-Trp-Asn-Tyr-NH$_2$, (SEQ ID NO: 3)

Arg-Glu-Trp-Gln-Phe-Tyr-Cys-NH$_2$, (SEQ ID NO: 4)

Arg-Glu-Trp-Gln-Phe-Tyr-Cys(Cys)-(NH$_2$), (SEQ ID NO: 5)

Asp-Arg-Glu-Trp-Gln-Phe-NH$_2$, (SEQ ID NO: 6)

Asp-Arg-Gln-Trp-Asn-Tyr-Ala-Cys-NH$_2$, (SEQ ID NO: 7)

Asp-Arg-Gln-Trp-Asn-Tyr-Ala-Cys(Cys)-(NH$_2$), (SEQ ID NO: 8)

Asp-Arg-Glu-Trp-Gln-Phe-Tyr-Cys-NH$_2$, (SEQ ID NO: 9)

Asp-Arg-Glu-Trp-Gln-Phe-Tyr-Cys(Cys)-(NH$_2$), (SEQ ID NO: 10)

Asp-Arg-Gln-Trp-Lys-Phe-NH$_2$, (SEQ ID NO: 11)

Arg-Glu-Trp-Gln-Phe-Tyr-NH$_2$. (SEQ ID NO: 12)

3. The peptide of claim 1, wherein said peptide of general formula (I) is solubilized in one or more physiologically acceptable solvents selected from the group consisting of water, glycerol, ethanol, propanediol, butylene glycol, dipropylene glycol, the ethoxylated or propoxylated diglycols, the cyclic polyols, and mixtures of these solvents.

4. A cosmetic composition comprising:
a peptide of general formula (I):

$$R_1\text{-}(AA)_n\text{-}X_1\text{-}Arg\text{-}X_2\text{-}Trp\text{-}X_3\text{-}X_4\text{-}X_5\text{-}X_6(R_3)\text{-}(AA)_p\text{-}R_2$$

wherein, $X_1$ is aspartic acid or absent,
$X_2$ is glutamine or glutamic acid,
$X_3$ is asparagine or lysine or glutamine or absent,
$X_4$ is phenylalanine or tyrosine or absent,
$X_5$ is tyrosine or alanine or absent,
$X_6$ is cysteine or absent,
AA is any amino acid and n and p are integers between 0 and 2,
$R_1$ is the primary amine function of the N-terminal amino acid, free or substituted by a group of the acyl type (R—CO—) wherein the radical R is either a saturated or unsaturated $C_1$ to $C_{30}$ alkyl chain of the acetyl type, or an aromatic group of the benzoyl, tosyl, or benzyloxycarbonyl type,
$R_2$ is the hydroxyl group of the carboxyl function of the C-terminal amino acid, substituted by a group chosen from a $C_1$ to $C_{30}$ alkyl chain, or an $NH_2$, NHY or NYY group with Y representing a $C_1$ to $C_4$ alkyl chain or one of the salts thereof, $R_3$ is the thiol function of cysteine in the $X_6$ position, wherein the thiol function is free or substituted by a methyl group or an acetyl group, or the thiol function is covalently bound by a disulfide bond to another cysteine; and a physiologically acceptable medium,
wherein said peptide of formula (I) is a dermatopontin-activating agent; and
with the proviso that when $X_1$ is absent, n is 0.

5. The composition of claim 4, wherein said peptide is present in a concentration of between $10^{-9}$ M and $10^{-3}$ M with respect to the total weight of the composition.

6. The composition of claim 4 wherein the composition is suitable for topical administration.

7. The composition of claim 4 further comprising at least one other active agent.

8. The composition of claim 4, wherein said peptide is present in a concentration of between $10^{-8}$ M and $10^{-5}$ M with respect to the total weight of the composition.

9. The composition of claim 4, wherein said peptide of general formula (I) is

```
                                           (SEQ ID NO: 1)
Asp-Arg-Gln-Trp-NH2, (SEQ ID NO: 2)
Asp-Arg-Glu-Trp-NH2, (SEQ ID NO: 3)
Asp-Arg-Gln-Trp-Asn-Tyr-NH2, (SEQ ID NO: 4)
Arg-Glu-Trp-Gln-Phe-Tyr-Cys-NH2, (SEQ ID NO: 5)
Arg-Glu-Trp-Gln-Phe-Tyr-Cys(Cys)-(NH2), (SEQ ID NO: 6)
Asp-Arg-Glu-Trp-Gln-Phe-NH2, (SEQ ID NO: 7)
Asp-Arg-Gln-Trp-Asn-Tyr-Ala-Cys-NH2, (SEQ ID NO: 8)
Asp-Arg-Gln-Trp-Asn-Tyr-Ala-Cys(Cys)-(NH2), (SEQ ID NO: 9)
Asp-Arg-Glu-Trp-Gln-Phe-Tyr-Cys-NH2, (SEQ ID NO: 10)
Asp-Arg-Glu-Trp-Gln-Phe-Tyr-Cys(Cys)-(NH2), (SEQ ID NO: 11)
Asp-Arg-Gln-Trp-Lys-Phe-NH2, (SEQ ID NO: 12)
Arg-Glu-Trp-Gln-Phe-Tyr-NH2.
```

10. The composition of claim 4, wherein said peptide of general formula (I) is solubilized in one or more physiologically acceptable solvents selected from the group consisting of water, glycerol, ethanol, propanediol, butylene glycol, dipropylene glycol, the ethoxylated or propoxylated diglycols, the cyclic polyols, and mixtures of these solvents.

11. A method of treating the cutaneous signs of aging and photoaging, the method comprising:
providing a composition comprising a peptide of general formula (I):

$$R_1-(AA)_n-X_1-Arg-X_2-Trp-X_3-X_4-X_5-X_6(R_3)-(AA)_p-R_2$$

wherein,
$X_1$ is aspartic acid or absent,
$X_2$ is glutamine or glutamic acid,
$X_3$ is asparagine or lysine or glutamine or absent,
$X_4$ is phenylalanine or tyrosine or absent,
$X_5$ is tyrosine or alanine or absent,
$X_6$ is cysteine or absent,
AA is any amino acid and n and p are integers between 0 and 2,
$R_1$ is the primary amine function of the N-terminal amino acid, free or substituted by a group of the acyl type (R—CO—) wherein the radical R is either a saturated or unsaturated $C_1$ to $C_{30}$ alkyl chain of the acetyl type, or an aromatic group of the benzoyl, tosyl, or benzyloxycarbonyl type,
$R_2$ is the hydroxyl group of the carboxyl function of the C-terminal amino acid, substituted by a group chosen from a $C_1$ to $C_{30}$ alkyl chain, or an $NH_2$, NHY or NYY group with Y representing a $C_1$ to $C_4$ alkyl chain or one of the salts thereof,
$R_3$ is the thiol function of cysteine in the $X_6$ position, wherein the thiol function is free or substituted by a methyl group or an acetyl group, or the thiol function is covalently bound by a disulfide bond to another cysteine; and
applying the composition to the skin before or after exposure to the sun;
with the proviso that when $X_1$ is absent, n is 0.

12. The method of claim 11, wherein the peptide is an active agent that increases the expression of proteins of the extracellular matrix by the fibroblasts of the skin or increases regeneration of the epidermis and dermis.

13. The method of claim 11, wherein applying occurs after exposure to sun, and the composition reduces degradation of collagen and elastic fibers in the skin.

14. The method of claim 11, wherein said peptide is present in a concentration of between $10^{-9}$ M and $10^{-3}$ M with respect to the total weight of the composition.

15. The method of claim 11, wherein said peptide of general formula (I) is

```
                                           (SEQ ID NO: 1)
Asp-Arg-Gln-Trp-NH2, (SEQ ID NO: 2)
Asp-Arg-Glu-Trp-NH2, (SEQ ID NO: 3)
Asp-Arg-Gln-Trp-Asn-Tyr-NH2, (SEQ ID NO: 4)
Arg-Glu-Trp-Gln-Phe-Tyr-Cys-NH2, (SEQ ID NO: 5)
Arg-Glu-Trp-Gln-Phe-Tyr-Cys(Cys)-(NH2), (SEQ ID NO: 6)
Asp-Arg-Glu-Trp-Gln-Phe-NH2, (SEQ ID NO: 7)
Asp-Arg-Gln-Trp-Asn-Tyr-Ala-Cys-NH2, (SEQ ID NO: 8)
Asp-Arg-Gln-Trp-Asn-Tyr-Ala-Cys(Cys)-(NH2), (SEQ ID NO: 9)
Asp-Arg-Glu-Trp-Gln-Phe-Tyr-Cys-NH2, (SEQ ID NO: 10)
Asp-Arg-Glu-Trp-Gln-Phe-Tyr-Cys(Cys)-(NH2),
```

-continued

Asp-Arg-Gln-Trp-Lys-Phe-NH$_2$, (SEQ ID NO: 11)

Arg-Glu-Trp-Gln-Phe-Tyr-NH$_2$. (SEQ ID NO: 12)

16. The method of claim 11, wherein said peptide of general formula (I) is solubilized in one or more physiologically acceptable solvents selected from the group consisting of water, glycerol, ethanol, propanediol, butylene glycol, dipropylene glycol, the ethoxylated or propoxylated diglycols, the cyclic polyols, and mixtures of these solvents.

* * * * *